United States Patent [19]
O'Lenick, Jr.

[11] Patent Number: 5,639,791
[45] Date of Patent: Jun. 17, 1997

[54] DI-GUERBET ESTERS IN PERSONAL CARE APPLICATIONS

[75] Inventor: Anthony J. O'Lenick, Jr., Lilburn, Ga.

[73] Assignee: Siltech Inc, Norcross, Ga.

[21] Appl. No.: 548,737

[22] Filed: Oct. 26, 1995

Related U.S. Application Data

[63] Continuation-in-part of Ser. No. 332,135, Oct. 31, 1994, Pat. No. 5,488,121.
[51] Int. Cl.$^6$ ........................................... A01N 37/02
[52] U.S. Cl. ..................... 514/552; 514/844; 514/847; 554/1; 554/167
[58] Field of Search ................ 554/167, 1; 514/552, 514/844, 847

[56] References Cited

U.S. PATENT DOCUMENTS

| | | | |
|---|---|---|---|
| 4,425,458 | 1/1984 | Lindner et al. | 524/314 |
| 4,868,236 | 9/1989 | O'Lenick | 524/308 |
| 5,488,121 | 1/1996 | O'Lenick | 554/167 |

*Primary Examiner*—Deborah D. Carr

[57] ABSTRACT

The present invention deals with the utilization of certain novel di-guerbet esters which are prepared by the reaction of a guerbet alcohol and a guerbet acid in personal care applications. These esters provide lubrication, solvent and dry feel attributes to personal care applications.

12 Claims, No Drawings

DI-GUERBET ESTERS IN PERSONAL CARE APPLICATIONS

RELATED APPLICATIONS

This application is a continuation in part of Ser. No. 08/332,135 filed Oct. 31, 1994, now U.S. Pat. No. 5,488,121.

BACKGROUND OF THE INVENTION

1. Field of the Invention

The present invention deals with a process for conditioning skin which comprises contacting the skin with an effective conditioning amount of certain novel di-guerbet esters which are prepared by the reaction of a guerbet alcohol and a guerbet acid. These materials have outstanding liquidity, lubricating properties, resistance to oxidation, and minimal variation in viscosity as a function of temperature is required. Hair and skin are effected by environmental conditions and become dry, course and . Conditioning, as used herein, means the process by which the hair and skin are repaired from the degradative processes. The hair and skin after a conditioning would be smoother, better hydrated, lubricated, moisturized and protected. The application of the esters of the present invention provide a thin film of an oily material to the hair and skin which allow the hair and skin to retain it's moisture, lubricate, soften and remoisturize the skin and hair.

2. Description of the Art Practices

Guerbet alcohols have been known for many years. Over the years there have been a number of derivatives patented.

U.S. Pat. No. 4,868,236 to O'Lenick discloses a guerbet citric ester and polymers thereof useful in plastic lubrication.

U.S. Pat. No. 4,425,458 to Lindner and O'Lenick teaches that specific guerbet esters can be used as polycarbonate lubricants.

None of these materials possess the critical di-guerbet linkage in the molecule. That is the molecules of the current invention have guerbet substitution patterns on both the alcohol and acid portion of the molecule and contain no ether linkages. Only with this specific linkages will the desired dryness on the skin, the desired solvent properties and the desired lubrication properties on hair and skin.

THE INVENTION

This invention relates to the use of a particular group of highly branched esters made by the reaction of a guerbet alcohol and a guerbet acid for conditioning skin in personal care applications.

Fatty acid esters are a class of compounds which find applications in many diverse segments of the chemical industry. Even within an industry segment, this class of compounds are used in a wide variety of different applications. Within the personal care market segments there are several applications in which esters are useful. The first class of esters are the simple esters which function as emmolients and conditioners. These esters are generally water insoluble, and are prepared by the reaction of an alcohol and a carboxylic acid. The second class of esters are modified by the incorporation of ethylene oxide into the alcohol prior to ethoxylation. They are surface active esters that possess properties like emulsification. This article will deal only with the first type of esters, that is the simple esters.

There are numerous applications in which it is desirable to have a simple ester which is very oily, and which contributes cushion to the skin. These esters feel in many regards like mineral oil. There are likewise applications in which it is desirable for the esters to dry rapidly, giving a talc like, silky feel to the skin. It is also desirable for esters to have solvent properties to remove make up.

The specific structure of the ester determines the functional attributes of the product. There are many possible structural variations which can impact upon the performance of esters. This paper will address two: (a) the presence of branching in the molecule, and (b) the location within the molecule in which the branching is located.

The esters based upon both linear alcohol and linear acid had the most drag on the skin. They likewise had the longest dry time, indicating little penetration.

The incorporation of a guerbet branch in the alcohol portion of the molecule decreased the drag, but still had a long dry time and did not give much penetration.

The use of a guerbet acid and a linear alcohol resulted in a product which still less drag, but retained a long dry time.

The ester, of the present invention, made with both a guerbet alcohol and guerbet acid, had almost no drag, and a fast dry time.

Solvent Properties

The esters based upon both linear alcohol and linear acid had little solvent properties when evaluated in removing lip stick.

The incorporation of a guerbet branch in the alcohol portion of the molecule had little affect upon solvent properties when evaluated in removing lip stick.

The use of a guerbet acid and a linear alcohol resulted in a slight improvement upon solvent properties when evaluated in removing lip stick.

The ester, of the present invention, made with both a guerbet alcohol and guerbet acid, had outstanding solvent properties when evaluated in removing lip stick.

The compounds of the current invention are specific di beta branched esters conforming to the following structure;

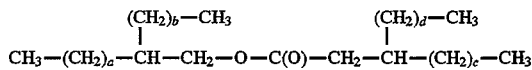

wherein a, b, c and d are independently integers ranging from 4 to 20.

Preferred Embodiment

In a preferred embodiment a, c and d are each 3.

In another preferred embodiment a, b , c and d are each 4.

In another preferred embodiment a, b, c and d are each 5.

In another preferred embodiment a, b c and d are each 6.

In another preferred embodiment a, b, c and d are each 7.

In another preferred embodiment a, b, c and d are each 14.

In still another preferred embodiment a and b are 14, and c and d are 3.

In still another preferred embodiment a and b are 8 and c and d are 4.

In still another preferred embodiment a and b are 7 and c and d are 5.

In still another preferred embodiment a and b are 5 and c and d are 8.

In still another preferred embodiment a and b are 4 and c and d are 8.

In still another preferred embodiment a and b are 3, and c and d are 14.

In a preferred embodiment the effective conditioning amount ranges from 0.1 to 100% by weight.

In a preferred embodiment the effective conditioning amount ranges from 5.0 to 20% by weight.

In a preferred embodiment the effective conditioning amount ranges from 0.5 to 50% by weight.

In a preferred embodiment the effective conditioning amount ranges from 10 to 20% by weight.

EXAMPLES

RAW MATERIALS

Guerbet Alcohols

Guerbet Alcohols are regiospecifically beta branched alcohols. They have been known since the 1890's when Marcel Guerbet first synthesized them. (M. Guerbet, C. R. Acad. Sci. Paris, 128, 511; 1002 (1899)). These materials are high in molecular weight and are liquid to very low temperatures. The guerbet reaction gives very specific branching in the alcohol as shown;

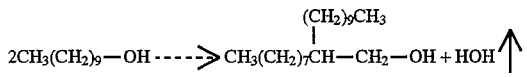

As can be seen by the above reaction the molecules have substitution on the second carbon from the hdroxyl group.

This branching has been found to be critical to the preparation of a product having the desired lubrication and oxidative stability properties. If the branching were on the same carbon as the hydroxyl group, the hydroxyl group would be a secondary one and would be very hindered and has low reactivity. As one moves the branch position away from the beta carbon, the liquidity, lubricity and metal substantivity decreases. If the branch is lower alkyl like methyl in some oxo alcohols, there is little increase in the liquidity, lubricity and metal substantivity over normal alcohols having the same number of carbons. Additionally, the oxo process gives only some beta branching (between 1 and 28%) the guerbet process gives essentially 100 % product.

Guerbet alcohols that are the reaction product of one specific raw material alcohol will result in a so called "homo-guerbet". In this case R and R' are identical. If the starting alcohols used in the guerbet reaction are of differing molecular weights a so called "hetero-guerbet" results. This type of guerbet has a mixed distribution of all possible combinations of alcohols. For this reason R and R' in the generic formula may be the same or different.

Guerbet alcohols are available commercially from Nova Molecular Technologies Janesville, Wis. They are marketed under the following commercial names:

| Example | Commercial Name | a | b |
| --- | --- | --- | --- |
| 1 | Nova Guerbet C10 | 3 | 3 |
| 2 | Nova Guerbet C12 | 4 | 4 |
| 3 | Nova Guerbet C14 | 5 | 5 |
| 4 | Nova Guerbet C16 | 6 | 6 |
| 5 | Nova Guerbet C18 | 7 | 7 |
| 6 | Nova Guerbet C20 | 8 | 8 |
| 7 | Nova Guerbet C32 | 14 | 14 |

Guerbet Acids

Guerbet alcohols are oxidized into acids having the same regiospecific beta branched properties. These properties present both in the acid and alcohol make products useful in the present invention.

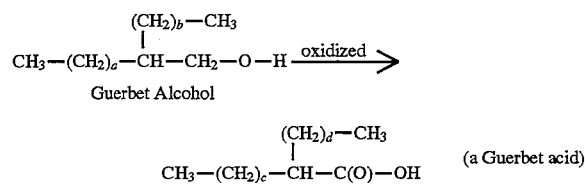

Vista Chemical practices the oxidation of guerbet alcohols commercially. The values of c and d were actually determined by analysis and are not dependant upon trade name for meaning.

| Example | Commercial Name | c | d |
| --- | --- | --- | --- |
| 8 | Isocarb 10 | 3 | 3 |
| 9 | Isocarb 12 | 4 | 4 |
| 10 | Isocarb 14 | 5 | 5 |
| 11 | Isocarb 16 | 6 | 6 |
| 12 | Isocarb 18 | 7 | 7 |
| 13 | Isocarb 20 | 8 | 8 |
| 14 | Isocarb 32 | 14 | 14 |

Isocarb is a trademark of Vista.

Di-guerbet Ester Synthesis

The esterification reaction is carried out using an excess of alcohol or acid or more typically using an equivalent of each. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

The di-guerbet ester is prepared by the esterification reaction as shown below:

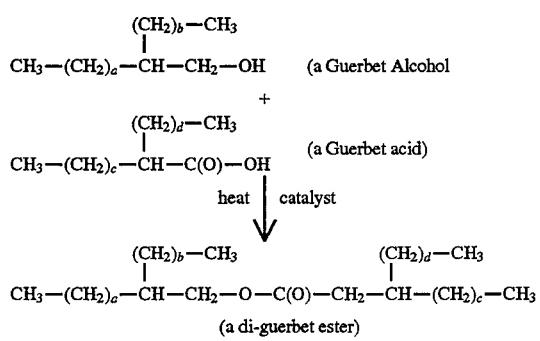

(a di-guerbet ester)

General Procedure

To the specified number of grams of guerbet alcohol (examples 1–7) is added the specified number of grams of the specified guerbet acid (Examples 8–16). Next add 0.1% stannous oxylate based upon the total weight of the batch after all ingredients have been charged, under agitation. The temperature of the mass is raised to 180°–200° C. and water is stripped off as formed. The acid value and hydroxyl value drop to vanishingly small values, and the saponification value increases to theoretical.

The products are clear liquids and are liquid to extraordinary temperatures. They exhibit outstanding lubrication properties and are outstanding viscosity index modifiers.

|  | Guerbet Alcohol | | Guerbet Acid | |
| --- | --- | --- | --- | --- |
| Example | Example | Grams | Example | Grams |
| 15 | 1 | 157.0 | 8 | 171.0 |
| 16 | 2 | 185.0 | 9 | 199.0 |
| 17 | 3 | 213.0 | 10 | 227.0 |
| 18 | 4 | 241.0 | 11 | 255.0 |
| 19 | 5 | 269.0 | 12 | 283.0 |
| 20 | 6 | 297.0 | 13 | 311.0 |
| 21 | 7 | 465.0 | 14 | 479.0 |
| 22 | 7 | 465.0 | 8 | 479.0 |
| 23 | 6 | 297.0 | 9 | 311.0 |
| 24 | 5 | 269.0 | 10 | 283.0 |
| 25 | 4 | 241.0 | 11 | 255.0 |
| 26 | 3 | 213.0 | 12 | 227.0 |
| 27 | 2 | 185.0 | 13 | 199.0 |
| 28 | 1 | 157.0 | 14 | 171.0 |

In order to compare the compounds of the present invention to related materials the following compounds were prepared:

Example 28

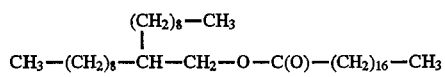

This material was prepared by the reaction of raw material example 6 with stearic acid. The resulting ester is only branched in the alcohol portion of the molecule.

Example 30

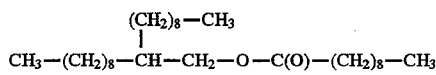

This material was prepared by the reaction of raw material example 6 with capric acid. The resulting ester is only branched in the alcohol portion of the molecule.

APPLICATIONS EXAMPLES

Dry Time

The time it took for 0.5 ml of ester applied to the skin to be "dry" was measured for the test esters.

| Designation | OH/AC Type | Dry Time | Comments |
| --- | --- | --- | --- |
| Class 1 (Products having 32 carbon atoms) | | | |
| Palmitic Palmitate | (L/L) | N/A | Solid |
| Hexyldecyl Palmitate | (G/L) | 48 sec | Slushy |
| Palmitic Hexyldecanonate | (L/G) | 15 sec | Liquid |
| Hexyldecyl hexyldecanonte | (G/G)* | 11 sec | Liquid |
| Class 2 (Products having 40 carbon atoms) | | | |
| Eicosanoyl Eicosanate | (L/L) | N/A | Solid |
| Octyldodecyl Eicosanate | (G/L) | 22 sec | Slushy |
| Eicosanoyl Octyldodecyonate | (L/G) | 56 sec | Slushy |
| Octyldodecyl Octyldodecyonate | (G/G)* | 10 sec | Liquid |

*products of the present invention.
L is linear; G is guerbet

Solvent Properties

The solvent properties of the esters was evaluated using the following formulation:

| Material | % |
| --- | --- |
| Ester | 3.0 |
| Cyclomethicone | 97.0 |
| Total | 100.0 |

In each evaluation 100% cyclomethicone was evaluated as a negative control. The test methodology was as follows:

A standard lipstick was chosen for evaluation. It was applied to the back of the hand in a two inch mark. 5 grams of the test solution was applied to a tissue and the lipstick was rubbed three times. The remaining lipstick if any was observed. The properties were evaluated on a scale of 1–10.

| Designation | OH/AC Type | Solvent Properties |
| --- | --- | --- |
| Class 1 (Products having 32 carbon atoms) | | |
| Palmitic Palmitate | (L/L) | 1 |
| Hexyldecyl Palmitate | (G/L) | 6 |
| Palmitic Hexyldecanonate | (L/G) | 7 |
| Hexyldecyl hexyldecanonte | (G/G)* | 10 |
| Class 2 (Products having 40 carbon atoms) | | |
| Eicosanoyl Eicosanate | (L/L) | 2 |
| Octyldodecyl Eicosanate | (G/L) | 6 |

| Designation | OH/AC Type | Solvent Properties |
|---|---|---|
| Eicosanoyl Octyldodecyonate | (L/G) | 7 |
| Octyldodecyl Octyldodecyonate | (G/G)* | 9 |

Rating System 0 (no removal) 10 Complete removal
*products of the present invention.

The compounds of the present invention provide conditionig to the hair and skin. Conditioning, as used herein, means the process by which the hair and skin are repaired from the degradative processes. The hair and skin after a conditioning would be smoother, better hydrated, lubricated, moisturized and protected. The application of the esters of the present invention provide a thin film of an oily material to the hair and skin which allow the hair and skin to retain it's moisture, lubricate, soften and remoisturize the skin and hair.

I claim:

1. A process for conditioning skin, in need thereof, which comprises contacting the skin with an effective conditioning amount of a di-guerbet ester conforming to the following structure:

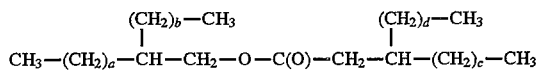

wherein a, b, c and d are independently integers ranging from 4 to 20.

2. A process claim 1 wherein a, b , c and d are each 4.
3. A process of claim 1 wherein a, b, c and d are each 5.
4. A process of claim 1 wherein a, b c and d are each 6.
5. A process of claim 1 wherein a, b, c and d are each 7.
6. A process of claim 1 wherein a, b, c and d are each 14.
7. A process of claim 1 wherein a and b are 8 and c and d are 4.
8. A process of claim 1 wherein a and b are 7 and c and d are 5.
9. A process of claim 1 wherein the effective conditioning amount ranges from 0.1 to 100% by weight.
10. A process of claim 1 wherein the effective conditioning amount ranges from 0.5 to 50% by weight.
11. A process of claim 1 wherein the effective conditioning amount ranges from 5 to 20% by weight.
12. A process of claim 1 wherein the effective conditioning amount ranges from 10 to 20% by weight.

* * * * *